(12) United States Patent
Chobotov

(10) Patent No.: US 12,213,897 B2
(45) Date of Patent: Feb. 4, 2025

(54) TANDEM MODULAR ENDOGRAFT

(71) Applicant: TriVascular, Inc., Santa Rosa, CA (US)

(72) Inventor: Michael V. Chobotov, Santa Rosa, CA (US)

(73) Assignee: TRIVASCULAR, INC., Santa Rosa, CA (US)

( * ) Notice: Subject to any disclaimer, the term of this patent is extended or adjusted under 35 U.S.C. 154(b) by 153 days.

(21) Appl. No.: 17/479,926

(22) Filed: Sep. 20, 2021

(65) Prior Publication Data

US 2022/0071785 A1 Mar. 10, 2022

Related U.S. Application Data

(63) Continuation of application No. 14/492,674, filed on Sep. 22, 2014, now Pat. No. 11,123,205.
(Continued)

(51) Int. Cl.
| A61F 2/07 | (2013.01) |
| A61F 2/06 | (2013.01) |
| A61F 2/848 | (2013.01) |
| A61F 2/856 | (2013.01) |
| A61F 2/89 | (2013.01) |

(52) U.S. Cl.
CPC ............ *A61F 2/856* (2013.01); *A61F 2/07* (2013.01); *A61F 2/848* (2013.01); *A61F 2/89* (2013.01); *A61F 2002/067* (2013.01); *A61F 2230/0034* (2013.01); *A61F 2230/0054* (2013.01); *A61F 2250/0003* (2013.01); *A61F 2250/0039* (2013.01); *A61F 2250/0069* (2013.01)

(58) Field of Classification Search
None
See application file for complete search history.

(56) References Cited

U.S. PATENT DOCUMENTS

| 5,316,023 A | 5/1994 | Palmaz et al. |
| 5,476,589 A | 12/1995 | Bacino |
(Continued)

FOREIGN PATENT DOCUMENTS

| CN | 1272053 A | 11/2000 |
| CN | 101917929 A | 12/2010 |
(Continued)

OTHER PUBLICATIONS

Chinese Office Action dated Feb. 27, 2017.
(Continued)

*Primary Examiner* — Ann Schillinger
(74) *Attorney, Agent, or Firm* — Foley & Lardner LLP

(57) ABSTRACT

A tandem modular endograft includes a main elongate tubular graft body having at least one circumferential inflatable channel disposed towards a proximal portion of the graft body wall and a plurality of circumferential inflatable channels disposed towards a distal portion of the graft body wall. A proximal expansion anchor is disposed at or secured to a proximal neck portion of the graft body wall. First and second elongate tubular stent-graft extensions may be percutaneously disposed into a distal end of the tubular graft body. In combination, proximal portions of the first and second stent-graft extensions are conformable to a shape of the open lumen of the main graft body.

20 Claims, 9 Drawing Sheets

Related U.S. Application Data

(60) Provisional application No. 61/881,491, filed on Sep. 24, 2013.

(56) References Cited

U.S. PATENT DOCUMENTS

| | | | |
|---|---|---|---|
| 5,507,769 A | 4/1996 | Marin et al. | |
| 5,639,278 A | 6/1997 | Dereume et al. | |
| 5,693,088 A * | 12/1997 | Lazarus | A61F 2/844 |
| | | | 623/1.35 |
| 6,129,756 A | 10/2000 | Kugler et al. | |
| 6,176,849 B1 | 1/2001 | Yang et al. | |
| 6,325,819 B1 | 12/2001 | Pavonik et al. | |
| 6,395,019 B2 * | 5/2002 | Chobotov | A61F 2/958 |
| | | | 623/1.36 |
| 6,610,035 B2 | 8/2003 | Yang et al. | |
| 6,673,103 B1 | 1/2004 | Golds et al. | |
| 6,776,604 B1 * | 8/2004 | Chobotov | B29C 66/8161 |
| | | | 425/522 |
| 6,958,212 B1 | 10/2005 | Hubbell et al. | |
| 7,090,693 B1 * | 8/2006 | Chobotov | B29C 66/8221 |
| | | | 623/1.36 |
| 7,125,464 B2 | 10/2006 | Chobotov et al. | |
| 7,147,660 B2 | 12/2006 | Chobotov et al. | |
| 7,147,661 B2 * | 12/2006 | Chobotov | A61F 2/915 |
| | | | 623/1.25 |
| 7,150,758 B2 * | 12/2006 | Kari | A61F 2/06 |
| | | | 623/1.25 |
| 7,314,483 B2 | 1/2008 | Landau et al. | |
| 7,481,836 B2 * | 1/2009 | Greenan | A61F 2/07 |
| | | | 623/1.53 |
| 7,744,912 B1 | 6/2010 | Hubbell et al. | |
| 8,206,427 B1 | 6/2012 | Ryan et al. | |
| 8,679,171 B2 | 3/2014 | Deem et al. | |
| 8,728,372 B2 | 5/2014 | Humphrey et al. | |
| 8,801,769 B2 * | 8/2014 | Chobotov | A61F 2/07 |
| | | | 623/1.36 |
| 9,144,486 B2 * | 9/2015 | Vinluan | A61F 2/07 |
| 9,993,328 B2 * | 6/2018 | Young | A61L 31/146 |
| 10,159,557 B2 * | 12/2018 | Chobotov | A61F 2/966 |
| 10,548,750 B2 * | 2/2020 | Chobotov | A61F 2/07 |
| 10,799,377 B2 * | 10/2020 | Vinluan | A61F 2/958 |
| 11,123,205 B2 * | 9/2021 | Chobotov | A61F 2/89 |
| 2002/0013620 A1 | 1/2002 | Kujawski | |
| 2003/0065377 A1 | 4/2003 | Davila et al. | |
| 2003/0120331 A1 | 6/2003 | Chobotov et al. | |
| 2005/0090804 A1 * | 4/2005 | Chobotov | A61F 2/07 |
| | | | 604/509 |
| 2005/0228484 A1 * | 10/2005 | Stephens | A61F 2/848 |
| | | | 623/1.21 |
| 2006/0222596 A1 | 10/2006 | Askari et al. | |
| 2006/0224232 A1 * | 10/2006 | Chobotov | A61F 2/07 |
| | | | 623/1.16 |
| 2009/0099649 A1 | 4/2009 | Chobotov et al. | |
| 2009/0204202 A1 | 8/2009 | Dierking et al. | |
| 2009/0319029 A1 * | 12/2009 | Evans | A61F 2/954 |
| | | | 623/1.35 |
| 2010/0063578 A1 | 3/2010 | Ren | |
| 2010/0305686 A1 | 12/2010 | Cragg et al. | |
| 2011/0130819 A1 | 6/2011 | Cragg et al. | |
| 2011/0257725 A1 * | 10/2011 | Argentine | A61F 2/07 |
| | | | 623/1.15 |
| 2013/0261734 A1 * | 10/2013 | Young | A61F 2/07 |
| | | | 623/1.22 |
| 2013/0268056 A1 | 10/2013 | Chobotov et al. | |
| 2013/0268057 A1 | 10/2013 | Vinluan et al. | |
| 2014/0222132 A1 | 8/2014 | Boucher et al. | |

FOREIGN PATENT DOCUMENTS

| | | |
|---|---|---|
| CN | 102076282 A | 5/2011 |
| JP | 2002-502629 A | 1/2002 |
| JP | 2010-540190 A | 12/2010 |
| JP | 2011-522614 A | 8/2011 |
| JP | 2013-512079 A | 4/2013 |
| WO | 9939662 A1 | 8/1999 |
| WO | 2009/046372 A2 | 4/2009 |

OTHER PUBLICATIONS

Chinese Office Action dated Aug. 20, 2020, from application No. 201480063739.5.

Chinese Office Action dated Dec. 16, 2020, from application No. 201480063739.5.

Chinese Office Action dated Dec. 27, 2019, from application No. 201480063739.5.

Chinese Office Action dated Dec. 8, 2017, from application serial No. 201480063739.5.

Chinese Office Action dated May 29, 2018, from application No. 201480063739.5.

European Office Action dated Mar. 11, 2021, from application No. 14782021.1.

Final Office Action dated Jun. 17, 2017, from U.S. Appl. No. 14/492,674.

Final Office Action dated Mar. 13, 2020, from U.S. Appl. No. 14/492,674.

Final Office Action dated Nov. 5, 2018, from U.S. Appl. No. 14/492,674.

Final Office Action dated Sep. 30, 2020, from U.S. Appl. No. 14/492,674.

Japanese Office Action dated Feb. 7, 2019, from application No. 2016-516890.

Japanese Office Action dated May 14, 2018, from application No. 2016-516890.

Japanese Office Action dated May 25, 2020, from application No. 2016-516890.

Non-Final Office Action dated Dec. 17, 2015, from U.S. Appl. No. 14/492,674.

Non-Final Office Action dated Mar. 29, 2018, from U.S. Appl. No. 14/492,674.

Non-Final Office Action dated Oct. 17, 2016, from U.S. Appl. No. 14/492,674.

Non-Final Office Action dated Sep. 12, 2019, from U.S. Appl. No. 14/492,674.

Notice of Allowance dated May 20, 2021, from U.S. Appl. No. 14/492,674.

PCT Search Report and Written Opinion Dated Dec. 11, 2014 for Counterpart PCT Application.

* cited by examiner

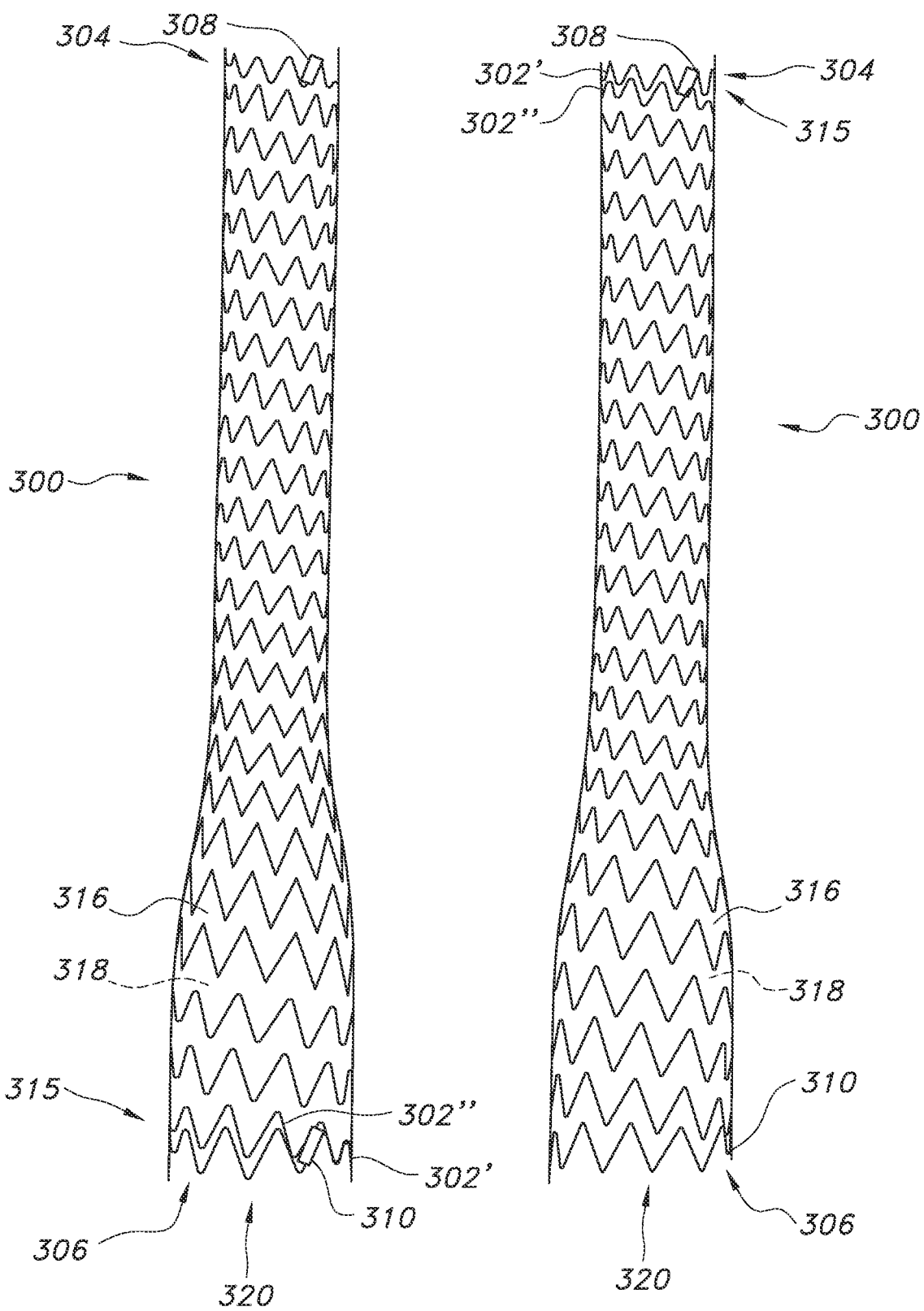

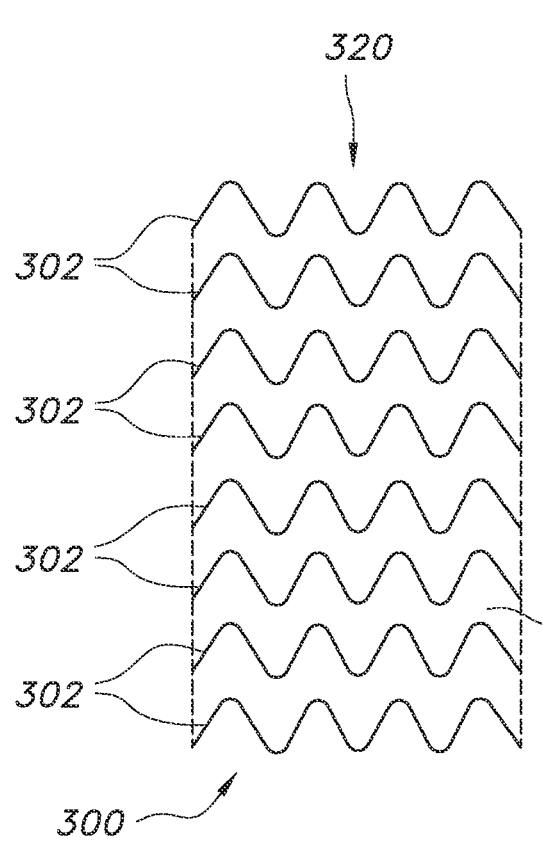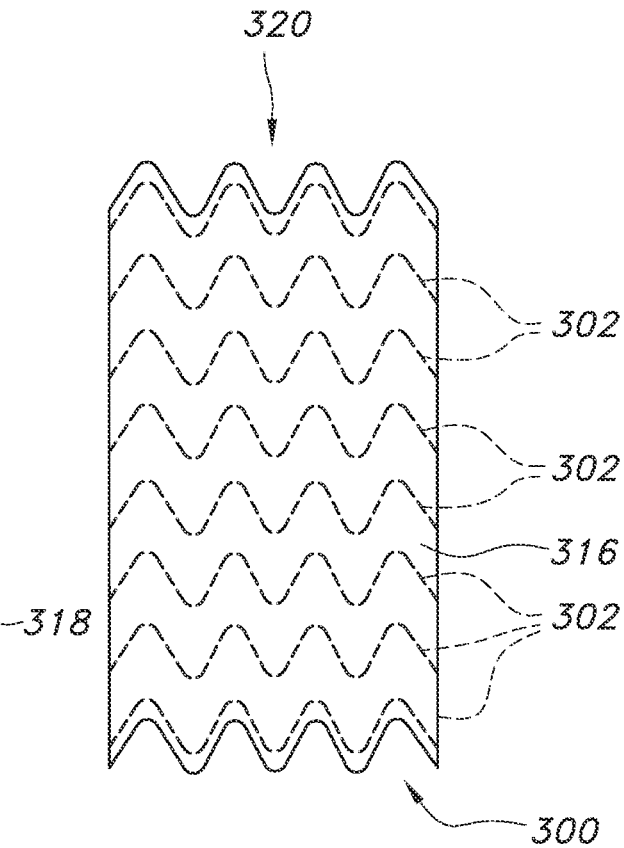
FIG. 9A  FIG. 9B
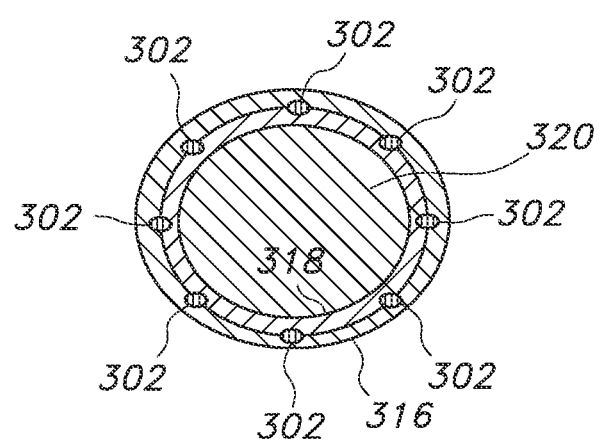
FIG. 10

TANDEM MODULAR ENDOGRAFT

CROSS-REFERENCE TO RELATED APPLICATIONS

This application is a continuation of U.S. application Ser. No. 14/492,674, filed Sep. 22, 2014, now U.S. Pat. No. 11,123,205, granted Sep. 21, 2021, which claims the benefit of U.S. Provisional Application No. 61/881,491, filed Sep. 24, 2013, the contents of which are incorporated herein by reference.

FIELD OF THE INVENTION

The present invention relates to endovascular graft systems for aneurysms involving major branch vessels. In particular, the present invention relates to a tandem modular endograft for treating aneurysms involving major branch vessels.

BACKGROUND OF THE INVENTION

The present invention relates to a system for the treatment of disorders of the vasculature, particularly aneurysms. An aneurysm is a medical condition indicated generally by an expansion and weakening of the wall of an artery of a patient. Aneurysms can develop at various sites within a patient's body. Thoracic aortic aneurysms (TAAs) or abdominal aortic aneurysms (AAAs) are manifested by an expansion and weakening of the aorta which is a serious and life threatening condition for which intervention is generally indicated. Existing methods of treating aneurysms include invasive surgical procedures with graft replacement of the affected vessel or body lumen or reinforcement of the vessel with a graft.

Surgical procedures to treat aneurysms can have relatively high morbidity and mortality rates due to the risk factors inherent to surgical repair of this disease, as well as long hospital stays and painful recoveries. Due to the inherent risks and complexities of surgical repair of aortic aneurysms, endovascular repair has become a widely used alternative therapy, most notably in treating AAAs. Early work in this field is exemplified by Lawrence, Jr. et al. in "Percutaneous Endovascular Graft: Experimental Evaluation", Radiology (May 1987) and by Mirich et al. in "Percutaneously Placed Endovascular Grafts for Aortic Aneurysms: Feasibility Study," Radiology (March 1989). Commercially available endoprostheses for the endovascular treatment of AAAs include the Endurant® stent graft system manufactured by Medtronic, Inc. of Minneapolis, Minn., the Zenith® stent graft system sold by Cook, Inc. of Bloomington, Ind., the PowerLink® stent graft system manufactured by Endologix, Inc. of Irvine, Calif., and the Excluder® stent graft system manufactured by W. L. Gore & Associates, Inc. of Newark, Del. A commercially available stent graft for the treatment of TAAs is the TAG™ system manufactured by W. L. Gore & Associates, Inc.

SUMMARY OF THE INVENTION

The present invention provides various graft assemblies for treatment of blood vessels, including modular graft assemblies, bifurcated graft assemblies, stent-graft assemblies, and combinations thereof. The present invention provides endovascular graft systems for aneurysms involving major branch vessels. In particular, the present invention provides a tandem modular endograft for treating aneurysms involving major branch vessels.

Some embodiments of a modular endovascular graft assembly include a main elongate tubular graft body having a proximal open end and an opposed distal open end, defining a graft body wall having a proximal portion, a medial portion, a distal portion and an open lumen therein between. The graft body wall may include a proximal neck portion disposed at the proximal end, at least one circumferential inflatable channel disposed towards the proximal portion of the graft body wall near the proximal open end of the main tubular graft body and distally prior the proximal neck portion, and/or a plurality of circumferential inflatable channels disposed towards the distal portion of the graft body wall near the distal open end of the main tubular graft body. A proximal expansion anchor may be disposed at or secured to the proximal neck portion of the graft body wall. First and second elongate tubular stent-graft extensions may be percutaneously disposed into the distal end of the tubular graft body, the first and second stent-graft extensions having respective proximal open ends and opposed distal open ends, defining graft body walls having a proximal portions, medial portions, distal portions and open lumens therein between. In combination, the proximal portions of the first and second stent-graft extensions are conformable to a shape of the open lumen of the main graft body.

The at least one circumferential inflatable channel may be disposed towards the proximal portion of the graft body and the plurality of circumferential inflatable channels disposed towards the distal portion of the graft body are in fluid communication with one and the other. The assembly may further include an inflation material for inflating the at least one circumferential inflatable channel disposed towards the proximal portion of the graft body and the plurality of circumferential inflatable channels disposed towards the distal portion of the graft body. The inflation material may be an in vivo curable material.

The first and second elongate tubular stent-graft extensions comprise a tubular stent may be securably disposed between a graft liner and a graft cover; the stent including an undulating wire having opposed first and second ends and being helically wound into a plurality of approximate circumferential windings to define a stent wall; the undulating wire having a plurality undulations defined by peaks and valleys with peaks of adjacent approximate circumferential windings being separated by a distance.

The graft liner may include at least one layer of porous PTFE having no discernable node and fibril structure. The graft covering may include at least one layer of porous PTFE having no discernable node and fibril structure. The graft body wall of the main tubular graft may include at least one layer of porous PTFE having no discernable node and fibril structure.

In combination, the proximal portions of the first and second stent-graft extensions may be conformable to the shape of the open lumen of the main graft body to prevent flow of bodily fluid between outer proximal portions of the first and second stent-graft extensions and the open lumen of the main tubular graft.

The open lumen of the main tubular graft may have approximately or substantially circular cross-section. The open lumens of the proximal portions of the first and second stent-graft extensions may have approximately or substantially circular cross-sections prior to being percutaneously disposed into the distal end of the tubular graft body. The open lumens of the proximal portions of the first and second stent-graft extensions, in combination, may have non-circular-shaped cross-sections after being percutaneously disposed into the distal end of the tubular graft body, such as but not limited to approximately or substantially D-shaped cross-sections.

The proximal expansion anchor may be a metallic member. The assembly metallic member may include a super elastic nitinol (NiTi) alloy. The proximal expansion anchor may be a dual stage member where a first crown portion having a first number of crowns and a second crown portion having a second number of crowns, where the first number of crowns may be the same as or different from the second number of crowns.

Some embodiments of a method of delivering a modular endovascular graft assembly may include providing the modular endovascular graft assembly according to the present invention; percutaneously delivering the main elongate tubular graft body and the proximal expansion anchor into a main bodily lumen having an aneurysm and having a first and second lumen branches; positioning the proximal expansion anchor and the at least one circumferential inflatable channel of the main graft body distally past the aneurysm; percutaneously delivering the first elongate tubular stent-graft extension into the distal end of the tubular graft body; and percutaneously delivering the second elongate tubular stent-graft extension into the distal end of the tubular graft body.

The method may further include expanding the proximal expansion anchor to secure the proximal expansion anchor to the bodily lumen. Moreover, the method may further include inflating the at least one circumferential inflatable channel of the main graft body with an inflation material to seal the main graft body against the bodily lumen. The method may include curing the inflation material.

The percutaneously delivery of the first and second elongate tubular stent-graft extensions may be approximately simultaneous. The distal portion of the first elongate tubular stent-graft extension may be disposed within the first lumen branch The distal portion of the second elongate tubular stent-graft extension may be disposed within the second lumen branch.

BRIEF DESCRIPTION OF THE DRAWINGS

FIGS. 6 and 7 depict various embodiments of stent structures useful in the present invention.

FIGS. 9A and 9B depict stent graft assemblies useful in the present invention.

FIG. 10 is a top cross sectional view of one embodiment of a stent graft assembly of the present invention.

DETAILED DESCRIPTION OF THE INVENTION

Figure 1:
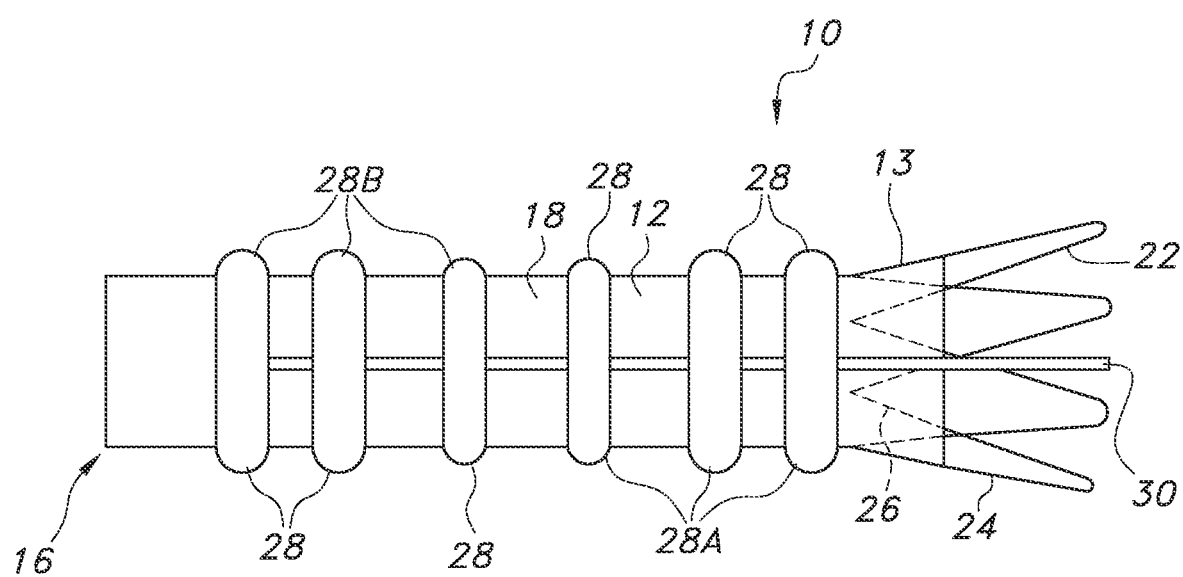
FIG. 1 is an elevation view of a graft assembly according to the present invention.

Embodiments of the invention are directed generally to methods and devices for treatment of fluid flow vessels with the body of a patient. Treatment of blood vessels is specifically indicated for some embodiments, and, more specifically, treatment of aneurysms, such as, but not limited to, thoracic aortic aneurysms and abdominal aortic aneurysms. The present invention provides various graft assemblies for treatment of blood vessels, including modular graft assemblies, bifurcated graft assemblies, stent-graft assemblies, and combinations thereof.

Modular graft assemblies of the present invention may include a main graft assembly having a network of inflatable channels and a graft. One end the graft assembly may include one or more graft extensions, disposed at, for example, a distal end of the assembly. The graft assembly may be bi-furcated. The graft assembly may be formed from a supple graft material, such as ePTFE, having a main fluid flow lumen therein. The graft assembly may include porous PTFE which has no discernable node and fibril structure. The bifurcated graft assembly may also include an ipsilateral leg with an ipsilateral fluid flow lumen in communication with the main fluid flow lumen, a contralateral leg with a contralateral fluid flow lumen in communication with the main fluid flow lumen, and a network of inflatable channels disposed on the main graft member. For some embodiments, the main graft member may have an axial length of about 5 cm to about 10 cm, more specifically, about 6 cm to about 8 cm in order to span an aneurysm of a patient's aorta without engaging the patient's iliac arteries directly with the legs of the main graft member.

The inflatable channels of the network of inflatable channels may be disposed on any portion of the graft assembly including the main body portion, as well as the ipsilateral and contralateral legs. The network of inflatable channels may be configured to accept a hardenable fill material to provide structural rigidity to the main graft member when the network of inflatable channels are in an inflated state and the inflation material has been cured or hardened. Radiopaque inflation material may be used to facilitate monitoring of the fill process and subsequent engagement of graft extensions. The network of inflatable channels may also include at least one inflatable cuff disposed on a proximal portion of the main graft member which is configured to seal against an inside surface of a patient's vessel, such as the aorta. The network of inflatable channels may include at least one longitudinal fill channel in communication with channels at the proximal and distal ends of the device. Further, the network of inflatable channels may include a longitudinal channel in communication with circumferential channels at one end of the device.

A proximal anchor member may be disposed at a proximal end of the main graft member and secured to the main graft member. The proximal anchor member has a self-expanding proximal stent portion secured to a self-expanding distal stent portion with struts. Some embodiments of the struts may have a cross sectional area that is substantially the same as or greater than a cross sectional area of proximal stent portions or distal stent portions adjacent the strut. Such a configuration may be useful in avoiding points of concentrated stress in the proximal anchor member or struts which couple components thereof. For some embodiments, the proximal stent of the proximal anchor member further includes a plurality of barbs having sharp tissue engaging tips that are configured to extend in a radial outward direction in a deployed expanded state. For some embodiments, the proximal anchor member includes a 4 crown proximal stent portion and an 8 crown distal stent portion which may be made from a super-elastic alloy such as super-elastic nitinol (NiTi) alloy.

The graft extensions may be disposed at the distal end of the main graft member. For a bifurcated graft assembly, at least one ipsilateral graft extension having a fluid flow lumen disposed therein may be deployed with the fluid flow lumen of the graft extension sealed to and in fluid communication with the fluid flow lumen of the ipsilateral leg of the main graft member. In addition, at least one contralateral graft extension having a fluid flow lumen disposed therein may be deployed with the fluid flow lumen of the graft extension sealed to and in fluid communication with the fluid flow lumen of the contralateral leg of the main graft member. For some embodiments, the graft extensions may include an interposed self-expanding stent disposed between at least one outer layer and at least one inner layer of supple layers of graft material. The interposed stent disposed between the outer layer and inner layer of graft material may be formed from an elongate resilient element helically wound with a plurality of longitudinally spaced turns into an open tubular configuration. In some embodiments, the interposed stent may have a winding, undulating configuration from the proximal end to the distal end. For some embodiments, the interposed stent is may include a super-elastic alloy such as super-elastic NiTi alloy. In addition, the graft material of each graft extension may further include at least one axial zone of low permeability for some embodiments.

Figure 2:
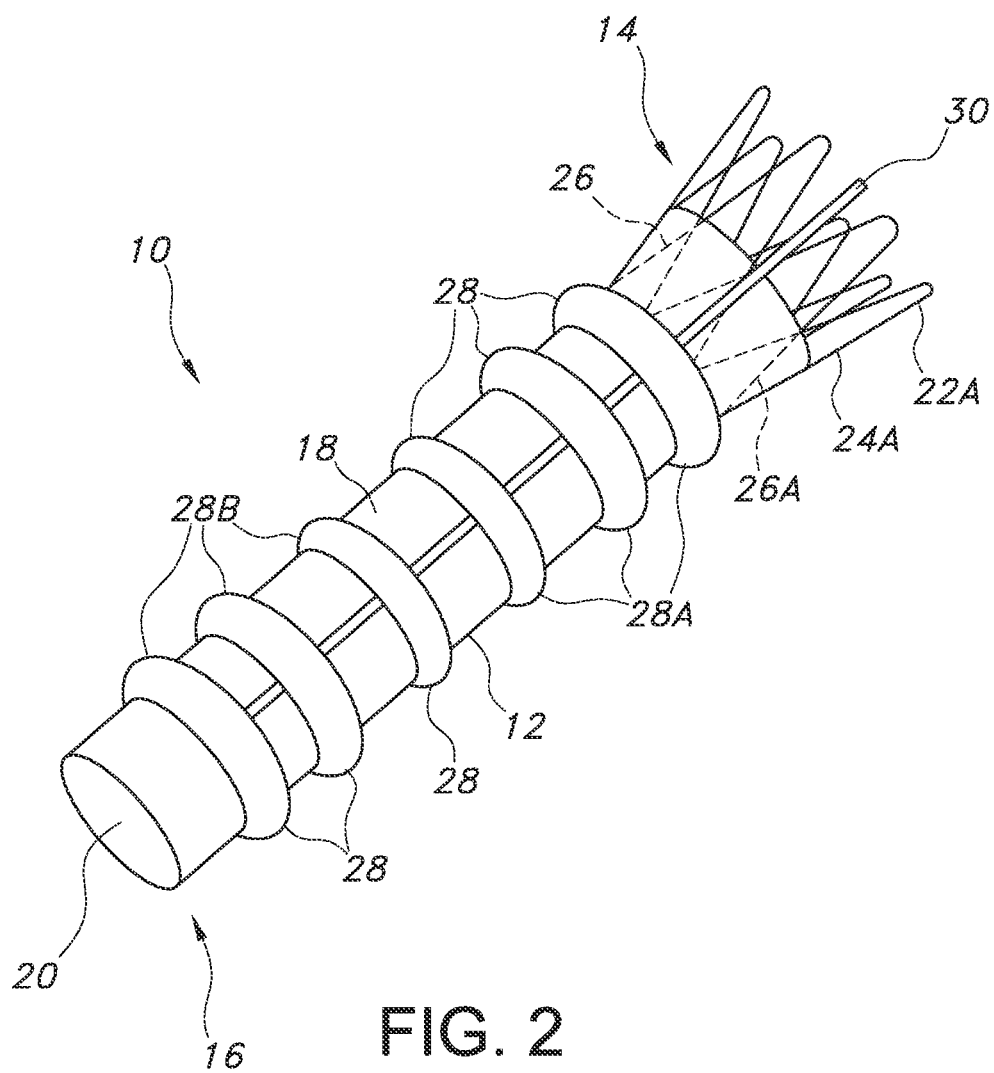
FIG. 2 is a perspective view of the graft assembly of FIG. 1.

FIGS. 1 and 2 depict a main graft assembly 10 for the treatment of an aneurysm. FIGS. 1 and 2 depict a main graft assembly 10 that is non-bifurcated. As depicted in FIGS. 1 and 2, the graft assembly 10 includes a main graft member 12 disposed between a proximal open end 14 and an opposed open distal end 16. The main graft 12 has a wall portion 18 that bounds a main fluid flow lumen 20 disposed therein and between the opposed open ends 14, 16. The graft wall portion 18 may be made from any biocompatible, durable material, including, for example, PTFE, Dacron, and the like. Unless otherwise specifically stated, the term "PTFE" as used herein includes PTFE, porous PTFE and ePTFE, any of which may be impermeable, semi-permeable, or permeable. Furthermore, the graft assembly 10 and any portions thereof including the main body and extensions described herein may include all PTFE, all ePTFE, or a combination thereof. In one particular embodiment, the graft wall portion 18 includes a porous PTFE material having no discernable node and fibril structure. Methods of formation of such materials include those methods described in U.S. Pat. No. 8,728,372 to Humphrey et al, entitled "PTFE Layers and Methods of Manufacturing", which is incorporated by reference in its entirety herein.

With regard to graft embodiments discussed herein, such as graft assembly 10, and components thereof, the term "proximal" refers to a location towards a patient's heart and the term "distal" refers to a location away from the patient's heart. With regard to delivery system catheters and components thereof discussed herein, the term "distal" refers to a location that is disposed away from an operator who is using the catheter and the term "proximal" refers to a location towards the operator.

Figure 3:
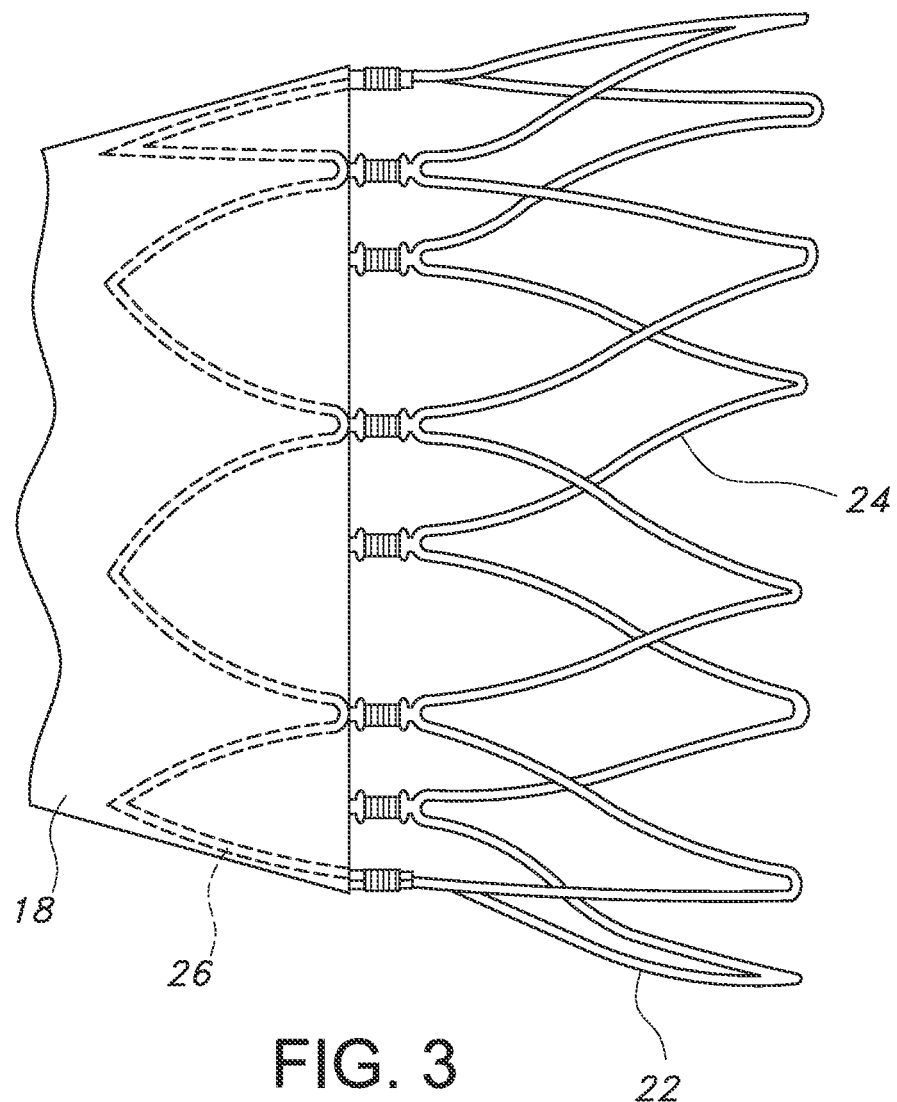
FIG. 3 is a close up view of a proximal anchor member and an optional connector ring of the graft assembly of FIG. 1.

The graft assembly 10 may include a proximal anchor member 22, which may be disposed at a proximal end 14 of the main graft 12, in particular at a neck portion 13 which is free of inflatable channels 28. One representative anchor system may include one as depicted in FIG. 3. The anchor member 22 includes a proximal stent 24, which may be self-expanding or may be balloon-expandable, that is formed from an elongate element having a generally serpentine shape with a number of crowns or apices at either end. As depicted in FIG. 2, six crowns or apices are shown for stent 24. The number of crowns or apices is not limiting and any suitable number may be used. As depicted in FIG. 3, eight crowns or apices may be used. Further, while the stent 24 is depicted as a single stage stent, the present invention is not so limited. Stent 24 may include two or more stages of interconnected stent portions. The number of crown in one stage may be the same or different from the number of crowns in another stage.

A distal end of the stent 24 may be mechanically coupled to a connector ring 26 which is embedded in graft material at the proximal end 14 of the main graft 12, or directly coupled to perforations in the proximal edge region of the main graft. Embodiments of the connector ring 26 may be generally circular in shape have regular undulations about the circumference that may be substantially sinusoidal in shape. U.S. Pat. No. 7,147,660, which is incorporated by reference herein, also includes anchor member embodiments that may be used for embodiments discussed herein.

The graft assembly 10 is not limited to the use of connector rings for securing anchor members to the graft portions of the graft assembly 10. Other securing techniques and securing members, such as those disclosed in U.S. Patent Application Publication No. 2013/0268056 to Chobotov et al., entitled "Low Profile Stent Graft and Delivery System"; and U.S. Patent Application Publication No. 2013/0268057 to Vinluan et al., entitled "Low Profile Stent Graft and Delivery System"; the entirety of each of which is incorporated herein by reference, may suitably be used.

Anchor member 22 may be configured as a self-expanding anchor member having an undulating pattern and may be made from stainless steel, nickel titanium alloy (NiTi), such as NITINOL, or any other suitable material. The anchor member 22 may be configured to be balloon expandable or self-expanding in an outward radial direction from a radially compressed state. The proximal anchor member 22 and its components may have the same or similar features, dimensions or materials to those of the stents described in U.S. Pat. No. 7,147,660 to Chobotov et al., entitled "Advanced Endovascular Graft", the content of which is hereby incorporated by reference in its entirety.

A network of inflatable elements or channels (generally depicted as reference numeral 28 in FIG. 1) is disposed on the graft body 12. The graft assembly 10 may include at least one proximal circumferential inflatable channel 28A and at least one distal circumferential inflatable channel 28B. The inflatable channels 28 may extend around the entire circumference of the graft body 12 or may only extend partially around the circumference of the graft body 12. The at least one proximal circumferential inflatable channel 28A and the at least one distal circumferential inflatable channel 28B may be in communication, for example fluid communication, with each other via a longitudinal inflatable fill channel 30. The longitudinal inflatable fill channel 30 is a tubular structure which is designed to allow communication between the interior of the inflatable channels 28A, 28B. The inflatable channels 28A, 28B may be inflated under pressure with an inflation material (not shown) through a longitudinal inflatable fill channel 30 that has a lumen disposed therein in fluid communication with the network of inflatable channels 28. The inflation material may be retained within the network of inflatable channels 28 by a one way-valve (not shown), disposed within the lumen of the longitudinal inflatable fill channel 30. The network of inflatable channels 28 may optionally be filled with a hardenable material that may be configured to harden, cure or otherwise increase in viscosity or become more rigid after being injected into the channels. Hardenable inflation materials such as gels, liquids or other flowable materials that are curable to a more solid or substantially hardened state may be used to provide mechanical support to the graft body 12 by virtue of the mechanical properties of the hardened material disposed within the channels 28. The network of inflatable channels 28 may also provide structural support to the graft body 12 when in an inflated state due to the stiffness of the channels created by the increased interior pressure within the channels even if a non-hardenable inflation material, such as saline or the like, is used so long as an increased interior pressure can be maintained. Such an increase in stiffness or rigidity may be useful for a variety of purposes. For example, during deployment, inflation of the network of inflatable channels 28 may urge the graft body 12 including the main flow channel and legs thereof to conform to a generally cylindrical configuration having open flow lumens which may be useful when attempting to locate and navigate the flow lumens of the graft assembly 10 with a delivery catheter, guidewire or the like. Such location and navigation of the flow lumens of the graft assembly 10 and portions thereof may also be facilitated by the use of radiopaque inflation materials that provide enhanced visualization under fluoroscopic imaging.

The network of inflatable channels 28 may include one or more circumferential channels disposed completely or partially about the graft body 12 as well as longitudinal or helical channels that may provide support as well as a conduit in communication with the circumferential channels 28 that may be used for filling the network of inflatable channels 28 with inflation material. Some embodiments may also employ radiopaque inflation material to facilitate monitoring of the fill process and subsequent engagement of graft extensions (when used). The network of inflatable channels 28 may also include one or more one or more enlarged circumferential channels in the form of inflatable cuffs. The inflatable cuff (or cuffs) is disposed towards the end of the graft body 12, such as at the proximal end 14 or distal end 16. One example of a proximal inflatable cuff is depicted in FIG. 2 as the circumferential inflatable channel 28A. An inflatable cuff or cuffs disposed at the ends of the body 12 may be configured to seal to an inside surface of a patient's vessel such as a patient's abdominal aorta. An inflatable cuff may be disposed on a portion of the main graft 12 distal of the proximal anchor member 22A and has an outer surface that extends radially from a nominal outer surface of the main graft 12. The inflatable cuff may be configured to expand radially beyond a nominal outer surface of the main graft 12 and provide a seal against an inside surface of a body lumen when the inflatable cuff is inflated with an inflation material to an expanded state. The axial separation of the proximal anchor member 22 and proximal inflatable cuff 28A allows for spatial separation of the primary anchoring mechanism and at least part of the sealing function which may allow the graft to be restrained or otherwise compressed to a smaller outer profile for deployment from a delivery catheter. An interior cavity of any inflatable channels 28 (including one or more inflatable cuffs) is in fluid communication with the interior cavity of the remaining network of inflatable channels 28 and may have a transverse dimension or inner diameter of about 0.040 inches to about 0.250 inches.

Some embodiments of main graft member 12 may include about 1 to about 8 circumferential inflatable channels disposed about the graft body 12. Some embodiments of the graft body 12 may include about 1 to about 4 longitudinal (or axial) inflatable fill channels 30 that may serve to connect the circumferential inflatable channels 28. Some embodiments of the circumferential channels 28 may extend a full circumference of the graft section upon which they are disposed, or they may extend only partially around the graft section upon which they are disposed. For the graft body embodiment 12 shown in FIGS. 1 and 2, the network of inflatable channels 28 includes an inflatable cuff (28A) disposed adjacent the proximal end 14 of the main body portion of the graft body 12. A longitudinal or axial channel extends substantially along the graft body 12 in fluid communication with the circumferential channels 28 and proximal inflatable cuff 28A at the proximal end of the graft body 12. The longitudinal inflatable channel 30 extends between and is in fluid communication with three of the distal inflatable channels 28B. As the inflation material is disposed through the longitudinal fill channel 30, each of the inflatable channels 28 (including proximal inflatable cuff 28A and distal inflatable channels 28B) are filled with inflation material. In addition, the longitudinal inflatable channel 30 is filled with inflation material, resulting in a rigid and strong graft assembly 10.

Some of the inflatable channels 28 of the graft assembly 10 discussed herein may be disposed circumferentially and axially. Alternatively, such inflatable channels 28 may be disposed in spiral, helical, or other configurations. Examples of channel configurations suitable for embodiments of the present invention are described further in U.S. Pat. No. 7,150,758 to Kari et al., entitled "Kink Resistant Endovascular Graft", the entirety of which is incorporated herein by reference. All inflatable channel embodiments described herein as circumferential, may alternatively take on any of the aforementioned alternative configurations. Other modular graft embodiments are discussed in U.S. Patent Application Publication No. 2006/0224232 to Chobotov, entitled "Hybrid Modular Endovascular Graft", which is hereby incorporated by reference herein in its entirety.

The network of inflatable channels 28, including an inflatable cuff and longitudinal inflatable channel 30, may be filled during deployment of the graft with any suitable inflation material. As discussed above, the inflation material may be used to provide outward pressure or a rigid structure from within the network of inflatable channels 28. Biocompatible gases, liquids, gels or the like may be used, including curable polymeric materials or gels, such as the polymeric biomaterials described in U.S. Pat. No. 7,744,912 and entitled "Biomaterials Formed by Nucleophilic Addition Reaction to Conjugated Unsaturated Groups" to Hubbell et al.; U.S. Pat. No. 6,958,212 and entitled "Conjugate Addition Reactions for Controlled Delivery of Pharmaceutically Active Compounds" to Hubbell et al.; and further discussed in U.S. Pat. No. 7,147,660 and entitled "Advanced Endovascular Graft" to Chobotov, et al., each of which is incorporated by reference herein in its entirety. Some embodiments may use inflation materials formed from glycidyl ether and amine materials, as discussed in U.S. Patent Application Publication No. 2006/0222596 and entitled "Non-Degradable, Low-Swelling, Water Soluble Radiopaque Hydrogel Polymer" to Askari et al., the contents of which are incorporated herein by reference. Some inflation material embodiments may include an in situ formed hydrogel polymer having a first amount of diamine and a second amount of polyglycidyl ether wherein each of the amounts are present in a mammal or in a medical device, such as an inflatable graft, located in a mammal in an amount to produce an in situ formed hydrogel polymer that is biocompatible and has a cure time after mixing of about 10 seconds to about 30 minutes and wherein the volume of said hydrogel polymer swells less than 30 percent after curing and hydration. Some embodiments of the inflation material may include radiopaque material such as sodium iodide, potassium iodide, barium sulfate, Visipaque 320, Hypaque, Omnipaque 350, Hexabrix and the like. For some inflation material embodiments, the polyglycidyl ether may be selected from trimethylolpropane triglycidyl ether, sorbitol polyglycidyl ether, polyglycerol polyglycidyl ether, pentaerythritol polyglycidyl ether, diglycerol polyglycidyl ether, glycerol polyglycidyl ether, trimethylolpropane polyglycidyl ether, polyethylene glycol diglycidyl ether, resorcinol diglycidyl ether, glycidyl ester ether of p-hydroxy benzoic acid, neopentyl glycol diglycidyl ether, 1,6-hexanediol diglycidyl ether, bisphenol A $(PO)_2$ diglycidyl ether, hydroquinone diglycidyl ether, bisphenol S diglycidyl ether, terephthalic acid diglycidyl ester, and mixtures thereof. For some inflation material embodiments, the diamine may be selected from (poly)alkylene glycol having amino or alkylamino termini selected from the group consisting of polyethylene glycol (400) diamine, di-(3-aminopropyl) diethylene glycol, polyoxypropylenediamine, polyetherdiamine, polyoxyethylenediamine, triethyleneglycol diamine and mixtures thereof. For some embodiments, the diamine may be hydrophilic and the polyglycidyl ether may be hydrophilic prior to curing. For some embodiments, the diamine may be hydrophilic and the polyglycidyl ether is hydrophobic prior to curing. For some embodiments, the diamine may be hydrophobic and the polyglycidyl ether may be hydrophilic prior to curing.

Other inflation materials that may be used for some embodiments include polyethylene oxide materials and neopentyl glycol diacrylate materials which are discussed in U.S. Pat. No. 6,610,035 to Yang et al., entitled "Hydrophilic Lubricity Coating for Medical Devices Comprising a Hybrid Top Coat", and U.S. Pat. No. 6,176,849 to Yang et al., entitled "Hydrophilic Lubricity Coating for Medical Devices Comprising a Hybrid Top Coat"; which are incorporated by reference herein in their entirety. U.S. Pat. No. 7,147,660 to Chobotov et al., entitled "Advanced Endovascular Graft", the contents of which are incorporated herein by reference, also includes inflation material embodiments that may be used for embodiments discussed herein.

Figures 4A, 4B:
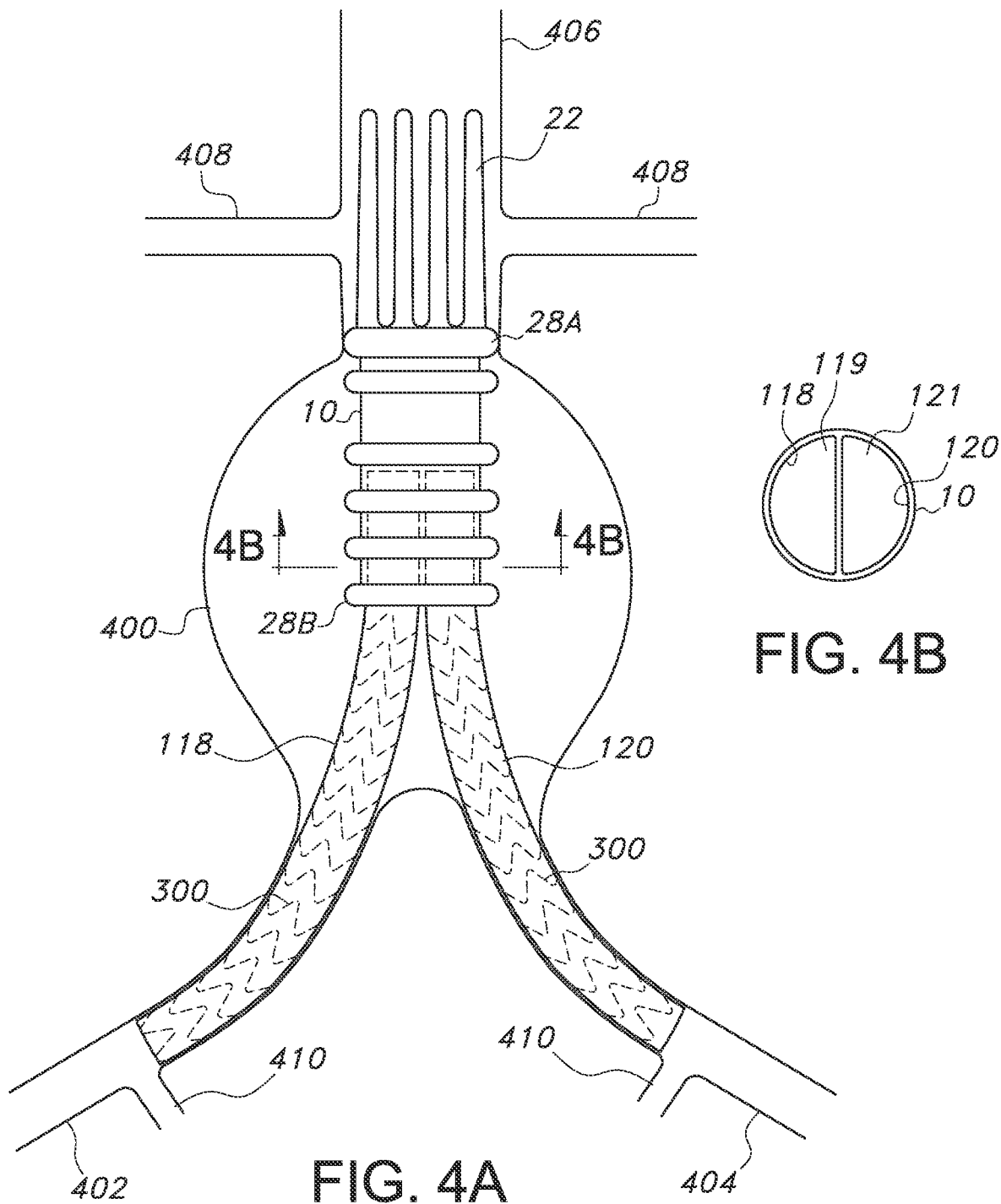
FIG. 4A depicts a bifurcated modular tandem graft assembly in its implanted state.
FIG. 4B is a cross-section view of the assembly of FIG. 4B taken along the 4B-4B axis of FIG. 4A.
Figure 5:
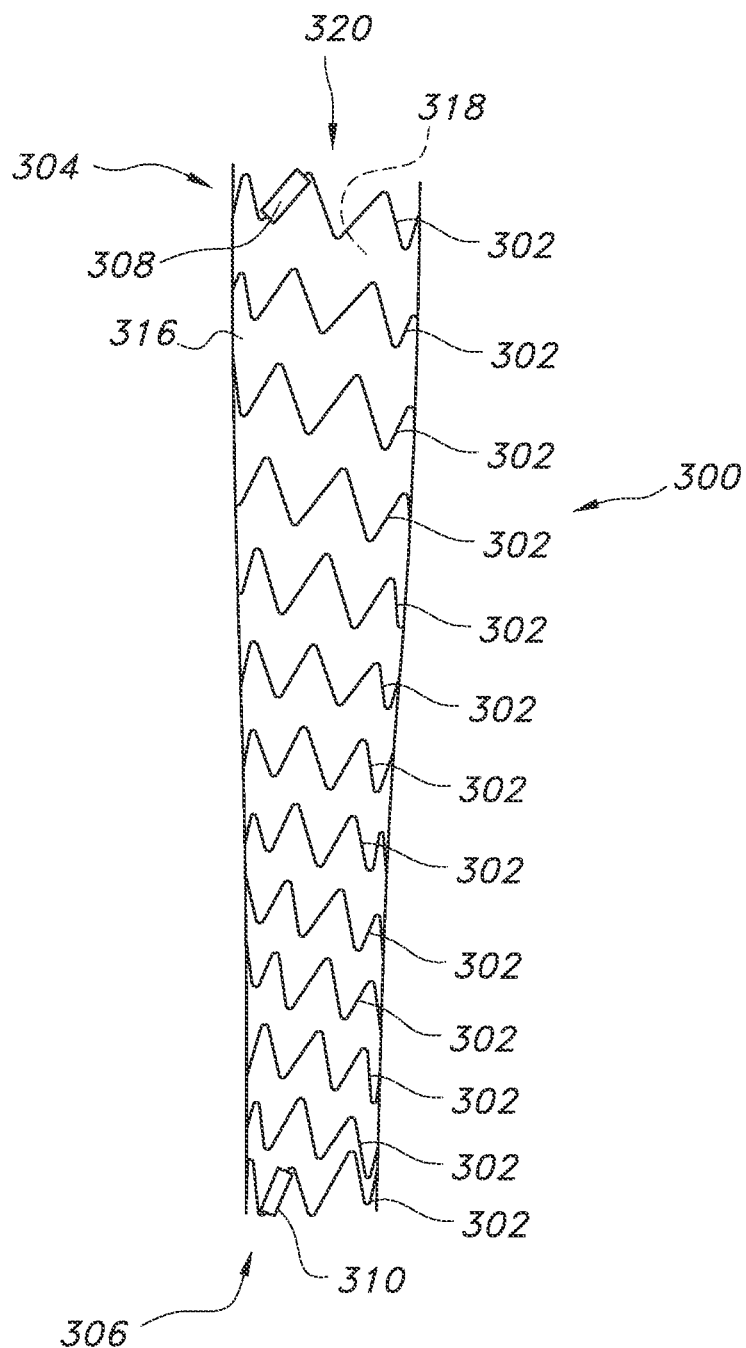
FIG. 5 depicts one embodiment of a stent structure useful in the present invention.

FIGS. 4A and 4B show a bifurcated modular tandem embodiment of a graft assembly 110 for treatment of an abdominal aortic aneurysm 400. The tandem graft assembly 110 includes the main graft assembly 10, a first modular branched leg or stent-graft extension 118 (having a first leg lumen 119) and a second modular branched leg or stent-graft extension 120 (having a second leg lumen 121). In some embodiments, the first branched leg 118 may be referred to as an "ipsilateral leg" 118, and the second branched leg 120 may be referred to as a "contralateral leg" 120.

The first and second graft legs 118 and 120 may be formed from an inner layer or layers and outer layer or layers of flexible graft material, such as PTFE or ePTFE. In one embodiment, the flexible graft material includes PTFE which is substantially porous but includes no discernable node and fibril structure. The inner and outer layers of graft material may be formed from tubular extrusions, laminated wraps of multiple layers of graft material or materials, and the like. The inner or outer layers of graft material may be permeable, semi-permeable or substantially non-permeable for some embodiments. For some embodiments, the nominal length of the legs 118 and 120 may be permeable with one or more longitudinal sections, such as a middle longitudinal section, being semi-permeable or non-permeable. Some embodiments of the graft legs 118 and 120 may have an overall tapered or flared configuration with a nominal inner lumen that tapers or flares when the graft extension is in a relaxed expanded state. For embodiments that include laminated wraps of material, the wraps may be carried out circumferentially, helically or in any other suitable configuration.

The first and second leg 118 and 120 are desirably stent-graft devices. A first radially expandable stent 300 may be interposed between an outer layer (not shown) and inner layer (not shown) of graft material for these legs. The interposed stent disposed between the outer layer and inner layer of graft material may be formed from an elongate resilient element helically wound with a plurality of longitudinally spaced turns into an open tubular configuration. The helically wound stent may be configured to be a self-expanding stent or radially expandable in an inelastic manner actuated by an outward radial force from a device such as an expandable balloon or the like. Some tubular prosthesis embodiments that may be used for graft extensions 118 and 120 are discussed in U.S. Pat. No. 6,673,103 to Golds et al., entitled "Mesh and Stent for Increased Flexibility", which is hereby incorporated by reference in its entirety herein.

Further details of the legs 118 and 120 as shown in more detail in FIGS. 5, 6, 7, 8A-8E, 9A, 9B and 10. As can be seen, a generally tubular stent 300 may be provided. The tubular stent 300 includes a helically-wound, undulating wire forming a series of adjacent helical windings 302, which may be made from the materials described above (including a resilient metal such as nitinol). The ends 304, 306 of the stent 300 may be secured to adjacent ring portions of the stent at distinct areas. For example, a first end may be adjoined via a first securement point 308, and a second end may be joined at a second securement point 310, as shown to avoid exposure of element ends to either PTFE graft material or possible patient tissues. In a preferred embodiment, the securement points 308, 310 are located proximal to the first end 304 and second end 306, respectively, with no other securement points on the stent 300. That is, aside from the helical windings 302 at the first end 304 (which may be referred to as a proximal end 304) and second end 306 (which may be referred to as a distal end 306), respectively, adjacent approximate circumferential windings 302 in the stent 300 may be free of interconnecting securement points. Any securement means may be used, including, for example, welding, such as struts and welds. It is desired that the relative stiffness of a stent be greater than the stiffness of the PTFE graft material so as to provide beneficial kink resistance.

The undulating wire may be a continuous element forming a series of helical windings 302 extending from one end 304 of the extension to the other end 306 thereof. The tubular stent 300 thus has an internal lumen 320 extending there through, from the first end 304 to the second end 306. The ends 304, 306 of the elongate element may be secured to adjacent ring members by any suitable means such as adhesive bonding, welding such as laser welding, soldering or the like. For some embodiments, the stent element may have a transverse dimension or diameter of about 0.005 inch to about 0.015 inch. As may be seen in FIGS. 6 and 7, the stent 300 may be tapered or flared. In addition, if desired, adjacent helical windings 302 may be arranged 315 such that adjacent helical windings 302 at one end (either the first end 304 or second end 306) have an acute angle formation at a portion of the stent 300 proximal to the end of the stent 300. That is, if desired, the helical winding closest to the end (shown as 302') may have an approximately 180° angle with respect to the longitudinal axis, while the helical winding next to this helical winding (shown as 302") has an angle less than 180°. These two helical windings (302' and 302") may be attached at securement points 308, 310.

Figures 8A, 8B:
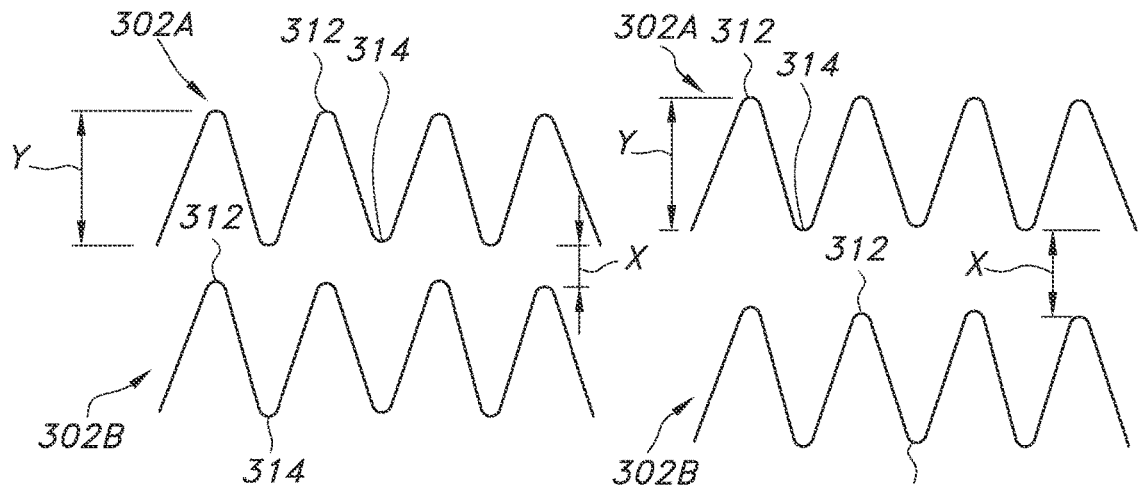
FIGS. 8A through 8E depict various arrangements of helically wound stents of the present invention.
Figures 8C, 8D:
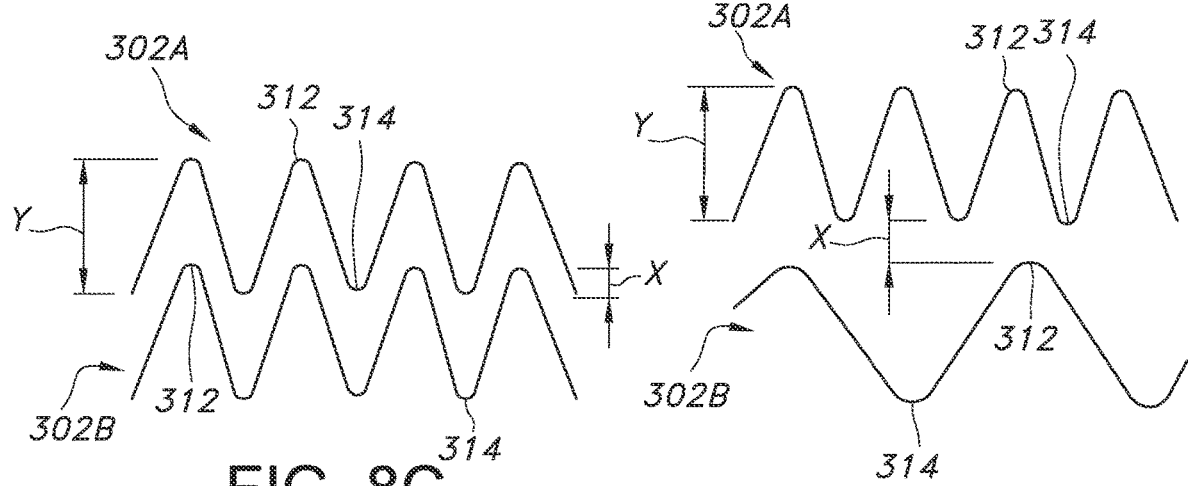
Figure 8E:
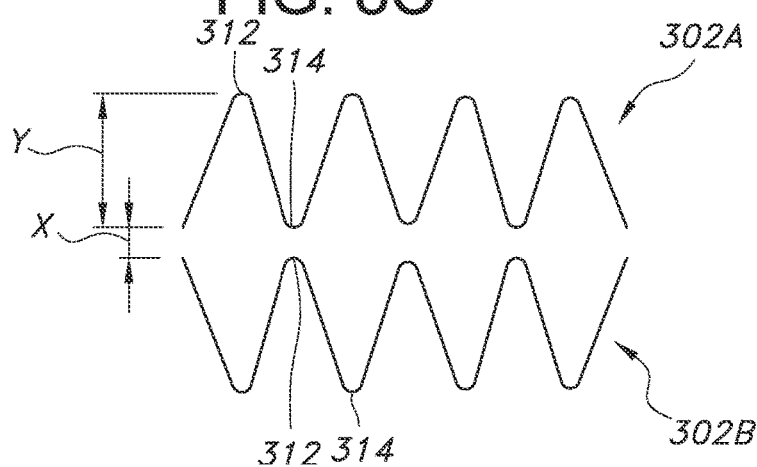

FIGS. 8A through 8E depicts various arrangements of the helical windings 302 formed by the undulating wire in forming the stent 300. Adjacent helical windings are depicted as 302A and 302B, but it will be understood that the arrangement depicted in FIGS. 8A through 8E may be applied to each helical winding 302 in the stent 300. Alternatively, the arrangements depicted in FIGS. 8A through 8E may be applied to only some of the helical windings 302 in the stent 300. Undulating wire of the stent 300 includes a series of peaks 312 and valleys 314 as the wire is helically wound. The arrangement of peaks 312 and valleys 314 may vary and may be arranged in any fashion desired. In some embodiments, such as that of FIG. 8A, the peaks 312 of one circumferential winding 302A may be substantially aligned with the peaks 312 of an adjacent circumferential winding 302B. As can be seen in FIG. 8B, the adjacent circumferential windings 302A and 302B may be spaced apart. As can be seen in FIG. 8C, the adjacent circumferential windings 302A and 302B may be closer together. In another embodiment, set forth in FIG. 8D, one peak 312 of one circumferential winding 302B may span two peaks 312 of an adjacent winding 302A. In another embodiment set forth in FIG. 8E, the peaks 312 of one circumferential winding 302A may be substantially aligned with the valleys 314 of an adjacent circumferential winding 302B. Other arrangements for the helical windings 302 are contemplated and will be readily understood by those of skill in the art.

The distances between adjacent windings 302A, 302B may vary along the length of the stent 300, where the distance at one end 304 is different than the distance at the second end 306. In each embodiment, there are two distances that should be considered. The first distance X is the distance between the lowest valley (314) of the first winding (302A) and the highest peak (312) of the second winding (302B). The second distance Y is the distance between the highest peak (312) and lowest valley (314) of the first winding (302A).

There may be at least two different ratios of X/Y (or equivalently X/Y) present in the device, including but limited to three different relative ratios of these distances X/Y. The first ratio is where X/Y is a relatively large positive number, that is, there is a relatively larger separation between the distance (X) as compared to the distance (Y). The second ratio is where X/Y is a relatively smaller positive number, that is, there is a relatively smaller separation between the distance (X) as compared to the distance (Y). Finally, the third ratio is where X/Y is a negative number, that is, the lowest peak of the first winding (302A) dips to a point lower than the highest peak of the second winding (302B). An example of a negative ratio is seen in FIG. 10C, where a negative value for X can be seen.

The ratio X/Y can be manipulated to obtain the desired properties of the stent graft in a local region. A relatively large X/Y ratio (preferably greater than about 0.5) produces a highly flexible region of a stent graft. A smaller X/Y ratio (preferably from about 0.1 to about 0.5) produces regions of a stent graft with moderate flexibility and moderate radial force. A region of a stent graft with an even smaller or negative X/Y ratio (preferably less than about 0.1) has a relatively high radial force with relatively less flexibility. The above ranges for X/Y are appropriate when the stent height Y is from about one-third of the diameter of the stent to about equal to the diameter of the stent. If Y is larger than this when compared to D, then the ranges for the X/Y ratios quoted above will be reduced. Similarly, if Y is much smaller than the stent diameter D, then the numerical values for the ranges above will be increased.

Using the principle described above, a stent graft can be constructed with varying ratios of X/Y along the length to achieve desired properties. For example, if a stent graft is used as an iliac limb in a modular endovascular graft for abdominal aortic aneurysms (AAAs), it may be desirable for the proximal end of the stent graft to have a relatively high radial force to maximize anchorage into the aortic body component of the modular system. In this case, the proximal end of the iliac limb could be designed with a small or negative X/Y ratio, such as −0.5, and Y may be chosen to be, for example, from about one fifth to one half of the stent graft diameter. In this region flexibility is less important than radial force so the negative X/Y ratio yields the desired properties. In the middle of the stent graft flexibility becomes important to accommodate the tortuous common iliac arteries often found in AAA patients. It may then be desirable to have a relatively large X/Y ratio, such as about 0.55, to achieve this flexibility. Near the distal end of the stent graft it may again be desirable to have more radial force to promote anchorage and sealing of the iliac limb into the common iliac artery of the patient, but not as much radial force as at the proximal end. In this case, it may be desirable to have an X/Y ratio near zero, or from about −0.1 to about 0.3.

Since the stent is formed in a helix along the length of the stent graft, it is possible to continuously vary the X/Y ratio to achieve the desired properties in various regions of the stent graft with smooth variations and no abrupt changes along the length. These smooth variations promote conformance to the vasculature and avoid the stress and/or strain concentrations and potential kinking that can result from abrupt transitions in mechanical properties along the length of a stent graft.

The stent 300 may include a longitudinal axis (generally defined along internal lumen 320) and a radial axis perpendicular to the longitudinal axis; where the helical windings 302 are wound at an acute winding angle of about 3 degrees to about 15 degrees with respect to the radial axis. As can be seen in FIGS. 6 and 7, the acute winding angle at a portion of the stent 300 proximal to the first end 304 is different from the acute winding angle at a portion of the stent 300 proximal to the second end 306. In some embodiments, a first helical winding 302 at the first end 304 may be perpendicular to the longitudinal axis. Further, it may be desired that a helical winding 302 at the second end 306 is perpendicular to the longitudinal axis. Helical windings 302 at the first end 304 and the second end 306 may both be perpendicular to the longitudinal axis, or only one may be perpendicular to the longitudinal axis. An adjacent peak 312 and an adjacent valley 314 of a helical winding 302 have a peak height from an apex of said adjacent peak to a base of said adjacent valley. It may be desired that the peak height at a portion of the stent 300 proximal to the first end 304 of the stent 300 is different from the peak height at a portion of the stent 300 proximal to the second end 306 of the stent 300.

At least one graft layer may be disposed on the stent 300. The placement of the graft layers may best be seen in FIGS. 9A, 9B and 10. In some embodiments, an inner graft layer 318 may be disposed on the interior surface of the helically wound stent 300, forming inner lumen 320. A second graft layer 316 may be disposed on the outer surface of the helically wound stent 300, forming an outside surface. More than one or two layers of graft material may be disposed on the interior or exterior of the helically wound stent 300 as desired. For some embodiments of first or second graft extensions 142, 144, layers of materials having different properties may be used in combination to achieve a desired clinical performance. For example, some layers of PTFE covering the stent 300 may be permeable, semi-permeable or substantially non-permeable depending on the desired performance and material properties. The layers 316 and 318 may be applied by a variety of methods and have a variety of configurations. For example, some layer embodiments may include extruded tubular structures applied axially over a mandrel or subassembly. Some layer embodiments 316 and 318 may be applied by wrapping layers circumferentially or wrapping tapes or ribbons in an overlapping helical pattern. For some embodiments, the outer layer 316 may be made from or include a semi-permeable or substantially non-permeable PTFE layer and the inner layer 318 may be made of or include a permeable layer of PTFE.

The first and/or second graft extensions 142, 144 may be made by forming the layers of material 316, 318 together with the helically wound stent 300 over a mandrel, such as a cylindrical mandrel (not shown). Once the innermost layer 316 of the extension 142, 144 has been wrapped about a shaped mandrel, a helical nitinol stent, such as helical stent 300, may be placed over the innermost layered PTFE layer 316 and underlying mandrel. If desired, one or more additional layers 318 of graft material may be wrapped or otherwise added over the exterior of the stent 300. If desired, the outer layer 318 may include low permeability PTFE film or PTFE film having substantially no permeability that does not have the traditional node fibril microstructure. The mandrel may then be covered with a flexible tube such that the layers 316, 318 and stent 300 are sandwiched under pressure and sintered so as to raise the temperature for the PTFE material to undergo a melt transformation in order to lock in its geometry and strength. The flexible tube (a manufacturing aid not shown) is removed from over the device and the resultant graft extension (142, 144) is removed from the mandrel.

The main graft 10 and graft portions of the first and second graft legs 118 and 120 may be made at least partially from polytetrafluoroethylene (PTFE) which may include expanded polytetrafluoroethylene (ePTFE). In particular, main graft 10 and graft legs 118 and 120 may include any number of layers of PTFE and/or ePTFE, including from about 2 to about 15 layers, having an uncompressed layered thickness of about 0.003 inches to about 0.015 inches for the supple graft material or materials alone without supporting or ancillary structures such as high strength stents, connector rings or the like. Such graft body sections may also include any alternative high strength, supple biocompatible materials, such as DACRON, suitable for graft applications. Descriptions of various constructions of graft body sections as well as other components of graft assembly 110 that may be used in any suitable combination for any of the embodiments discussed herein may be found in U.S. Pat. No. 7,125,464 to Chobotov et al., entitled "Method and Apparatus for Manufacturing an Endovascular Graft Section"; U.S. Pat. No. 7,090,693 to Chobotov et al., entitled "Endovascular Graft Joint and Method of Manufacture"; U.S. Pat. No. 7,147,661, entitled "Method and Apparatus for Shape Forming Endovascular Graft Material", to Chobotov et al.; U.S. Pat. No. 7,147,660 to by Chobotov et al., entitled "Advanced Endovascular Graft"; and U.S. Pat. No. 8,728,372 to Humphrey et al., entitled "PTFE Layers and Methods of Manufacturing"; the entirety of each of which is incorporated herein by reference.

Additional details of the above-described graft assemblies, including modular components, may be found in U.S. Patent Application Publication No. 2013/0261734 to Young et al., entitled "Advanced Kink Resistant Stent Graft"; the entirety of which is incorporated herein by reference.

Returning to FIGS. 4A, 4B, 11A, 11B and 11C, the tandem modular graft assembly offers advantages over systems of the prior art. For example, modular endografts typically employ a bifurcated main body section with separate lumens configured to receive one or more separate stent grafts to connect the main body section to distal branch arteries. The Ovation Abdominal Stent Graft System is an example of a tri-modular AAA system which employs a bifurcated main body section and two iliac limb stent grafts to bridge the main body to the iliac arteries. An alternative to this approach is to use a tubular main body section which can receive two or more stent grafts to bridge to various distal branch vessels. Using highly conformable stent grafts for these extension components can allow deploying two or more in the single open end of the main body. This allows for simplified manufacturing of the main body (avoiding the need to form a bifurcated structure), and also simplifies access or cannulation of the main body during deployment in the patient since a single large lumen is accessed as opposed to a smaller contralateral branch typically employed in modular AAA stent graft systems. The two limbs can be deployed simultaneously to ensure balanced "sharing" of the lumen by the stent grafts. Subsequent ballooning ("kissing balloons") can be employed to further balance the lumens and reduce the possibility for endoleaks at the junction ("type 3 endoleaks"). The main body can be constructed with inflatable annular rings along its length, and may also optionally include wire support elements. Making the mid part of the aortic body a little larger than its distal opening can further avoid the possibility of "limb steal" since the proximal ends of the limbs would be in a diameter large enough for both of their proximal ends to more fully expand, even if the two limbs are not deployed at exactly the same elevation (one more proximal than the other). Specifically for Ovation, making the aortic body with its distal end section about 17-18 mm in diameter (and constant at this diameter for a length of about 3-4 cm), two iliac limbs with 14 mm proximal ends would engage with adequate oversizing. Cannulation is greatly facilitated since the single large target lumen would be over 3 times larger in area than Ovation's contralateral gate currently sized at 9-11 mm. Furthermore, since there is only one large stable opening to access during cannulation, inadvertent access to the ipsilateral gate is not possible in this new single lumen configuration. No tether as employed by the Ovation system would be needed for contralateral leg stabilization (since there isn't a contra leg), so this would be a simplification of the delivery catheter. Additionally, there would be no need for rotational markers on the delivery system since the tubular aortic body can be made axisymmetric. Another benefit of this approach is that the device can be used as an AUI (aorto-uni iliac) device, ideal for ruptures or anatomy with severely diseased arteries on either iliac side.

Various methods of delivery systems and delivery of the device into a patient include those described in U.S. Patent Application Publication No. 2009/0099649 to Chobotov et al., entitled "Modular Vascular Graft for Low Profile Percutaneous Delivery", the contents of which are incorporated by reference in entirety herein. For endovascular methods, access to a patient's vasculature may be achieved by performing an arteriotomy or cut down to the patient's femoral artery or by other common techniques, such as the percutaneous Seldinger technique. For such techniques, a delivery sheath (not shown) may be placed in communication with the interior of the patient's vessel such as the femoral artery with the use of a dilator and guidewire assembly. Once the delivery sheath is positioned, access to the patient's vasculature may be achieved through the delivery sheath which may optionally be sealed by a hemostasis valve or other suitable mechanism. For some procedures, it may be necessary to obtain access via a delivery sheath or other suitable means to both femoral arteries of a patient with the delivery sheaths directed upstream towards the patient's aorta. In some applications a delivery sheath may not be needed and a delivery catheter may be directly inserted into the patient's access vessel by either arteriotomy or percutaneous puncture.

Figure 11A:
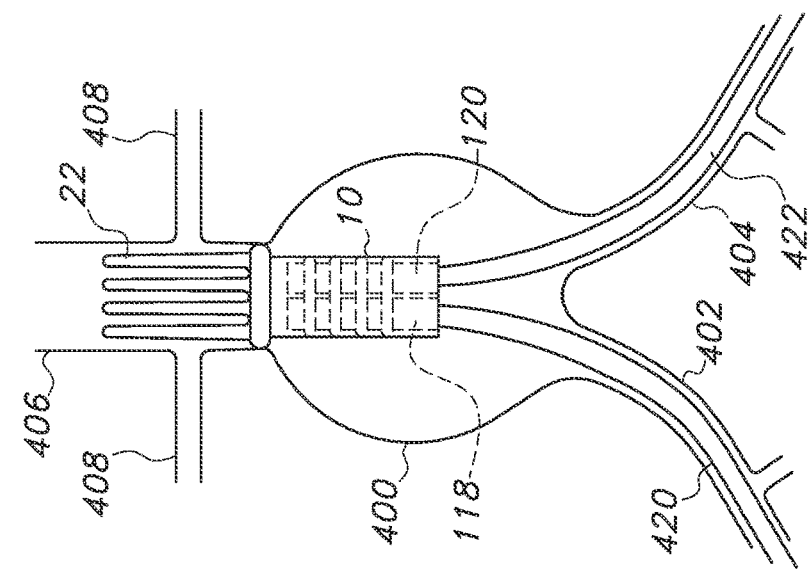
FIGS. 11A, 11B and 11C depict deployment stages of the assembly of FIG. 4A.

FIG. 11A depicts the initial placement of the modular endovascular graft assembly 110 of the present invention within a patient's vasculature. The modular endovascular graft assembly 110 may be advanced along a first guidewire (not shown) proximally upstream of blood flow into the vasculature of the patient including iliac arteries 402, 404 and aorta 406 shown in FIG. 11A. While the iliac arties 402, 404 may be medically described as the right and left common iliac arteries, respectively, as used herein iliac artery 402 is described as an ipsilateral iliac artery and iliac artery 404 is described as a contralateral iliac artery. The flow of the patient's blood (not shown) is in a general downward direction in FIG. 11A. Other vessels of the patient's vasculature shown in FIG. 11A include the renal arteries 408 and hypogastric arteries 410.

The modular endovascular graft assembly 110 may be advanced into the aorta 406 of the patient until the endovascular prosthesis 10 is disposed substantially adjacent an aortic aneurysm 400 or other vascular defect to be treated. The portion of the endovascular delivery system that is advanced through bodily lumens is a low profile delivery system; for example, having an overall outer diameter of less than 14 French. Other diameters are also useful, such as but not limited to less than 12 French, less than 10 French, or any sizes from 10 to 14 French or greater.

Figure 11B:
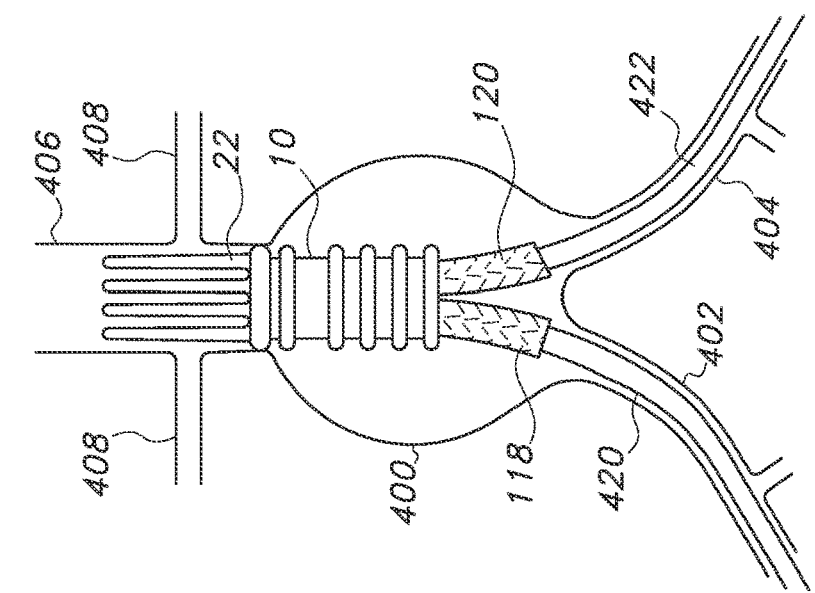
Figure 11C:
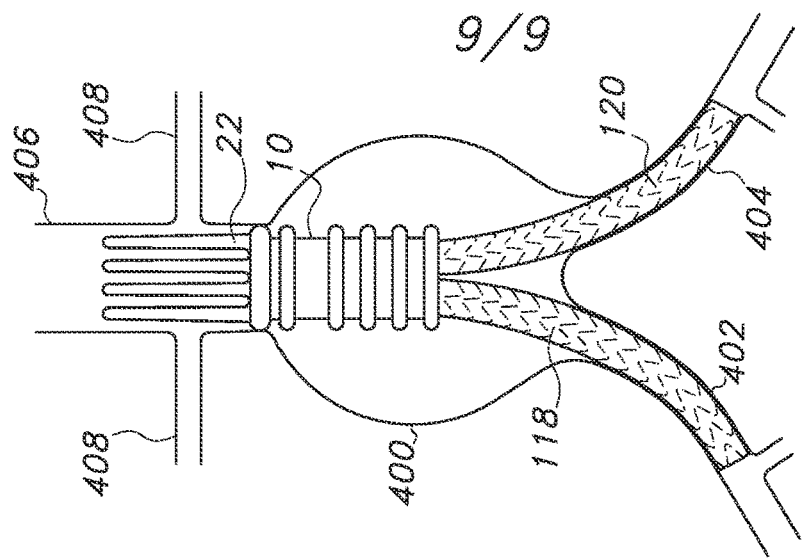

The proximal anchor member 22 is positioned across the renal arteries 408 to maintain blood there through. The anchor member 22 serves to anchor the graft assembly within the aorta 406. The proximal circumferential inflatable channel 28A of the main graft body 10 is placed beyond the aneurysm 400 in the aorta 406. Upon inflation of the proximal circumferential inflatable channel 28A, this inflated channel seals blood flow, if desired, from the aneurysm 400. As depicted in FIGS. 11A, 11B and 11C, after the main graft body 10 and anchor member 22 are deployed, the modular graft extension legs 118, 120 are deployed. The modular graft extension leg 118 is deployed through the iliac artery 402 via catheter 420, and the modular graft extension leg 120 is deployed through the iliac artery 404 via catheter 422. The modular graft extension legs 118, 120 may be deployed in separate stages or substantially and/or approximately in a simultaneous manner. The proximal ends 304 of the modular graft extension legs 118, 120 are disposed within the distal end portion 16 of the graft body 12. Upon expansion of the stents 300 within the modular graft extension legs 118, 120 and upon inflation of the distal inflatable channels 28B, the modular graft extension legs 118, 120 conform to the shape of the graft 10 in vivo to provide a modular assembly. The distal ends 306 of the modular graft extension legs 118, 120 are deployed within the respective iliac arteries 402, 404, as depicted in FIG. 11C.

The following embodiments or aspects of the invention may be combined in any fashion and combination and be within the scope of the present invention, as follows:

Embodiment 1. A modular endovascular graft assembly (110) comprising:
- a main elongate tubular graft body (10, 12) having a proximal open (14) end and an opposed distal open end (16), defining a graft body wall (18) having a proximal portion, a medial portion, a distal portion and an open lumen (20) therein between;
- the graft body wall (18) comprising a proximal neck portion (13) disposed at the proximal end (14);
- the graft body wall (18) comprising at least one circumferential inflatable channel (28A) disposed towards the proximal portion of the graft body wall (18) near the proximal open end (14) of the main tubular graft body (10, 12) and distally prior the proximal neck portion (13);
- the graft body wall (18) comprising a plurality of circumferential inflatable channels (28B) disposed towards the distal portion of the graft body wall (18) near the distal open end (16) of the main tubular graft body (10, 12);
- a proximal expansion anchor (22) disposed at or secured to the proximal neck portion (13) of the graft body wall (18);
- a first and second elongate tubular stent-graft extensions (118, 120, 300) percutaneously disposed into the distal end (16) of the tubular graft body (10, 12), the first and second stent-graft extensions (118, 120, 300) having respective proximal open ends (304) and opposed distal open ends (306), defining graft body walls having a proximal portions, medial portions, distal portions and open lumens (119, 121, 320) therein between;
- wherein, in combination, the proximal portions of the first and second stent-graft extensions (118, 120, 300) are conformable to a shape of the open lumen (20) of the main graft body (10, 12).

Embodiment 2. The assembly (110) of embodiment 1, wherein the at least one circumferential inflatable channel (28A) disposed towards the proximal portion of the graft body (10, 12) and the plurality of circumferential inflatable channels (28B) disposed towards the distal portion of the graft body (10, 12) are in fluid communication with one and the other.

Embodiment 3. The assembly (110) of any of the preceding embodiments, further comprising an inflation material for inflating the at least one circumferential inflatable channel (28A) disposed towards the proximal portion of the graft body (10, 12) and the plurality of circumferential inflatable channels (28B) disposed towards the distal portion of the graft body (10, 12).

Embodiment 4. The assembly (110) of embodiment 3, wherein the inflation material is an in vivo curable material.

Embodiment 5. The assembly (110) of any of the preceding embodiments, wherein the first and second elongate tubular stent-graft extensions (118, 120) comprise a tubular stent (300) securably disposed between a graft liner (318)

and a graft cover (316); the stent (300) comprising an undulating wire having opposed first and second ends and being helically wound into a plurality of approximate circumferential windings (302) to define a stent wall; the undulating wire having a plurality undulations defined by peaks and valleys with peaks of adjacent approximate circumferential windings being separated by a distance.

Embodiment 6. The assembly (110) of embodiment 5, wherein the graft liner (318) comprises at least one layer of porous PTFE having no discernable node and fibril structure.

Embodiment 7. The assembly (110) of embodiment 5, wherein; the graft covering (316) comprises at least one layer of porous PTFE having no discernable node and fibril structure.

Embodiment 8. The assembly (110) of any of the preceding embodiments, wherein the graft body wall (18) of the main tubular graft (10, 12) comprises at least one layer of porous PTFE having no discernable node and fibril structure.

Embodiment 9. The assembly (110) of any of the preceding embodiments, wherein, in combination, the proximal portions of the first and second stent-graft extensions (118, 120) are conformable to the shape of the open lumen (20) of the main graft body (10, 12) to prevent flow of bodily fluid between outer proximal portions of the first and second stent-graft extensions (118, 120) and the open lumen (20) of the main tubular graft (10, 12).

Embodiment 10. The assembly (110) of any of the preceding embodiments,
  wherein the open lumen (20) of the main tubular graft (10, 12) has approximately or substantially circular cross-section;
  wherein the open lumens (119, 121) of the proximal portions of the first and second stent-graft extensions have approximately or substantially circular cross-sections prior to being percutaneously disposed into the distal end (16) of the tubular graft body (10, 12); and
  wherein the open lumens (119, 121) of the proximal portions of the first and second stent-graft extensions (118, 120), in combination, have non-circular-shaped cross-sections after being percutaneously disposed into the distal end (16) of the tubular graft body (10, 12).

Embodiment 11. The assembly (110) of any of the preceding embodiments,
  wherein the open lumen (20) of the main tubular graft (10, 12) has approximately or substantially circular cross-section;
  wherein the open lumens (119, 121) of the proximal portions of the first and second stent-graft extensions (118, 120) have approximately or substantially circular cross-sections prior to being percutaneously disposed into the distal end (16) of the tubular graft body (10, 12); and
  wherein the open lumens (119, 121) of the proximal portions of the first and second stent-graft extensions (118, 120) have approximately or substantially D-shaped cross-sections after being percutaneously disposed into the distal end (16) of the tubular graft body (118, 120).

Embodiment 12. The assembly (110) of any of the preceding embodiments, wherein the proximal expansion anchor (22) is a metallic member.

Embodiment 13. The assembly (110) of embodiment 12, wherein the metallic member comprises a super elastic nitinol (NiTi) alloy.

Embodiment 14. The assembly (110) of any of the preceding embodiments, wherein the proximal expansion anchor (22) is a dual stage member where a first crown portion having a first number of crowns and a second crown portion having a second number of crowns, where the first number of crowns may be the same as or different from the second number of crowns.

Embodiment 15. A method of delivering a modular endovascular graft assembly (110), comprising:
  providing the modular endovascular graft assembly (110) of embodiment 1;
  percutaneously delivering the main elongate tubular graft body (10, 12) and the proximal expansion anchor (22) into a main bodily lumen (406) having an aneurysm (400) and having a first and second lumen branches (402, 404);
  positioning the proximal expansion anchor (22) and the at least one circumferential inflatable channel (28A) of the main graft body (10, 12) distally past the aneurysm (400);
  percutaneously delivering the first elongate tubular stent-graft extension (118) into the distal end (16) of the tubular graft body (10, 12); and
  percutaneously delivering the second elongate tubular stent-graft extension (120) into the distal end (16) of the tubular graft body (10, 12).

Embodiment 16. The method of embodiment 15, further comprising:
  expanding the proximal expansion anchor (22) to secure the proximal expansion anchor (22) to the bodily lumen (406).

Embodiment 17. The method of any of the embodiments 15 to 16, further comprising:
  inflating the at least one circumferential inflatable channel (28A) of the main graft body (10, 12) with an inflation material to seal the main graft body (10, 12) against the bodily lumen (406).

Embodiment 18. The method of any of the embodiments 15 to 17, further comprising:
  curing the inflation material.

Embodiment 19. The method of any of the embodiments 15 to 18, wherein the percutaneously delivery of the first and second elongate tubular stent-graft extensions (118, 120) are approximately simultaneous.

Embodiment 20. The method of any of the embodiments 15 to 19,
  wherein the distal portion of the first elongate tubular stent-graft extension (118) is disposed within the first lumen branch (402); and
  wherein the distal portion of the second elongate tubular stent-graft extension (120) is disposed within the second lumen branch (404).

While various embodiments of the present invention are specifically illustrated and/or described herein, it will be appreciated that modifications and variations of the present invention may be effected by those skilled in the art without departing from the spirit and intended scope of the invention. Further, any of the embodiments or aspects of the invention as described in the claims or in the specification may be used with one and another without limitation.

The invention claimed is:

1. A modular endovascular graft assembly comprising:
  a main elongate tubular graft body having a proximal open end and an opposed distal open end, defining a graft body wall having a proximal portion, a medial portion, a distal portion, and an open lumen therein between;

a proximal expansion anchor disposed at or secured to a proximal neck portion disposed at the proximal portion of the graft body wall;
a first and second elongate tubular stent-graft extensions percutaneously disposed into the distal open end of the main tubular graft body, the first and second stent-graft extensions having respective proximal open ends and opposed distal open ends, defining graft body walls having proximal portions, medial portions, distal portions, and open lumens therein between;
wherein, in combination, the proximal portions of the first and second stent-graft extensions are conformable to a shape of the open lumen of the main graft body; and
wherein the graft body wall of the main tubular graft body further comprises:
at least one circumferential inflatable channel disposed near but proximal to the distal open end of the main tubular graft body, wherein each of the at least one circumferential inflatable channel surrounds both the first and second elongate tubular stent-graft extensions when the first and second elongate tubular stent-graft extensions are percutaneously disposed into the distal open end of the main tubular graft body, causing the first and second stent-graft extensions to be secured to each other and to the graft body wall at the distal open end of the main tubular graft body when the at least one circumferential inflatable channel disposed near the distal portion of the main tubular graft body is in an inflated state.

2. The assembly of claim 1, wherein the at least one circumferential inflatable channel is in fluid communication with a single longitudinal inflatable fill channel and disposed towards the proximal portion of the main tubular graft body, the at least one circumferential inflatable channel in fluid communication with a plurality of circumferential inflatable channels.

3. The assembly of claim 2, further comprising an inflation material for inflating the at least one circumferential inflatable channel disposed near but proximal to the distal open end of the main tubular graft body and the plurality of circumferential inflatable channels disposed towards the distal portion of the graft body, the inflation material delivered to the at least one circumferential inflatable channel from the single longitudinal inflatable fill channel.

4. The assembly of claim 1, wherein the at least one circumferential inflatable channel encloses a portion of the first and second elongate tubular stent-graft extensions.

5. The assembly of claim 1, wherein the first and second elongate tubular stent-graft extensions comprise a tubular stent securably disposed between a graft liner and a graft cover, wherein the graft liner comprises at least one layer of porous PTFE having no discernable node and fibril structure.

6. The assembly of claim 5, wherein the graft cover comprises at least one layer of porous PTFE having no discernable node and fibril structure.

7. The assembly of claim 1, wherein the graft body wall of the main tubular graft body comprises at least one layer of porous PTFE having no discernable node and fibril structure.

8. The assembly of claim 1, wherein the proximal expansion anchor is a metallic member.

9. The assembly of claim 8, wherein the metallic member comprises a super elastic nitinol (NiTi) alloy.

10. The assembly of claim 1, wherein the proximal expansion anchor comprises a dual stage member with a first crown portion having a first number of crowns and a second crown portion having a second number of crowns, where the first number of crowns may be same as or different from the second number of crowns.

11. The assembly of claim 1, wherein the first and second elongate tubular stent-graft extensions comprise a tubular stent, the stent comprising an undulating wire having a plurality of approximate circumferential windings to define a stent wall, the undulating wire having a plurality of undulations defined by peaks and valleys with peaks of adjacent approximate circumferential windings being separated by a distance (X), and peaks of one circumferential winding being substantially aligned with peaks of an adjacent winding;
wherein an adjacent peak and an adjacent valley of said undulating wire has a peak height (Y) from an apex of said adjacent peak to a base of said adjacent valley;
wherein a ratio of the distance between adjacent peaks to the peak height (X/Y) at the proximal portions of the first and second stent-graft extensions is about 0.1 or less than 0.1.

12. The assembly of claim 11, wherein the ratio of the distance between adjacent peaks to the peak height (X/Y) at the distal portions of the first and second stent-graft extensions is about 0.5 or greater than 0.5.

13. The assembly of claim 11, wherein the ratio of the distance between adjacent peaks to the peak height (X/Y) at the medial portions of the first and second stent-graft extensions is from about 0.1 to about 0.5.

14. The assembly of claim 11, wherein the peak height (Y) of the first and second stent-graft extensions is from about one fifth to about one half of a diameter of the first and second stent-graft extensions.

15. The assembly of claim 1, wherein both the first and second elongate tubular stent-graft extensions are percutaneously disposed into the same distal open end of the main tubular graft body at the distal open end of the main tubular graft body.

16. A modular endovascular graft assembly comprising:
a main elongate tubular graft body having a proximal open end and an opposed distal open end, defining a graft body wall having a proximal portion, a medial portion, a distal portion, and an open lumen therein between;
the graft body wall comprising a proximal portion disposed at the proximal open end; the graft body wall comprising at least one proximal circumferential inflatable channel disposed towards the proximal portion of the graft body wall near the proximal open end of the main tubular graft body and distally prior the proximal portion of the graft body wall;
the graft body wall comprising a plurality of distal circumferential inflatable channels disposed towards the distal portion of the graft body wall near the distal open end of the main tubular graft body at least one of the plurality of distal circumferential inflatable channels disposed near but proximal to the distal open end of the main elongate tubular graft body;
a first and second elongate tubular stent-graft extensions separate from the main graft body, percutaneously disposed into the distal end of the tubular graft body, the first and second stent-graft extensions having respective proximal open ends and opposed distal open ends, defining graft body walls having a proximal portions, distal portions and open lumens therein between;
wherein each of the plurality of distal circumferential inflatable channels surrounds both the first and second elongate tubular stent-graft extensions when the first and second elongate tubular stent-graft extensions are percutaneously disposed into the distal end of the tubular graft body, wherein the plurality of distal circumferential inflatable channels causes the first and second stent-graft extensions to be secured to each other and to the main graft body at the distal end of the tubular graft body when the plurality of the distal circumferential inflatable channels is in an inflated state.

17. The assembly of claim 16, wherein at least one circumferential inflatable channel disposed near but proximal to the distal open end of the main tubular graft body encloses a portion of the first and second elongate tubular stent-graft extensions.

18. The assembly of claim 16, wherein the plurality of distal circumferential inflatable channels provide structural rigidity to the distal portion when the plurality of distal circumferential inflatable channels are in an inflated state.

19. The assembly of claim 16, wherein the plurality of proximal circumferential inflatable channels provide structural rigidity to the proximal portion when the plurality of proximal circumferential inflatable channels are in an inflated state.

20. The assembly of claim 16, wherein the at least one proximal circumferential inflatable channel is in fluid communication with a single longitudinal inflatable fill channel and disposed towards the proximal portion of the main tubular graft body, the at least one proximal circumferential inflatable channel in fluid communication with the plurality of distal circumferential inflatable channels.

\* \* \* \* \*